United States Patent [19]

Wasielewski et al.

[11] Patent Number: 5,539,100
[45] Date of Patent: Jul. 23, 1996

[54] ORGANIC SOLID STATE SWITCHES INCORPORATING PORPHYRIN COMPOUNDS AND METHOD FOR PRODUCING ORGANIC SOLID STATE OPTICAL SWITCHES

[75] Inventors: Michael R. Wasielewski, Naperville; George L. Gaines, River Forest; Mark P. Niemczyk, Wheaton; Douglas G. Johnson, Grayslake; David J. Gosztola, Bolingbrook, all of Ill.; Michael P. O'Neil, San Leandro, Calif.

[73] Assignee: The United States of America as represented by the United States Department of Energy, Washington, D.C.

[21] Appl. No.: 84,093

[22] Filed: Jul. 1, 1993

[51] Int. Cl.$^6$ .................. C07D 487/22; H01L 31/04
[52] U.S. Cl. ............................ 540/145; 524/88
[58] Field of Search ............................ 540/145

[56] References Cited

U.S. PATENT DOCUMENTS

| | | | |
|---|---|---|---|
| 4,281,645 | 8/1981 | Jöbsis | 128/2 R |
| 4,515,882 | 8/1985 | Mammino et al. | 430/58 |
| 4,534,015 | 8/1985 | Wilson et al. | 365/106 |
| 4,567,125 | 1/1988 | Moroni | 430/58 |
| 4,574,366 | 3/1988 | Potember et al. | 365/106 |
| 4,613,541 | 9/1988 | Isada | 428/212 |
| 4,627,029 | 12/1988 | Wilson | 365/107 |
| 4,704,353 | 11/1987 | Humphries et al. | 435/4 |
| 4,728,593 | 3/1988 | Freilich et al. | 430/72 |
| 4,731,756 | 3/1988 | Potember et al. | 365/153 |
| 4,792,208 | 12/1988 | Ulman et al. | 350/96.14 |
| 4,849,330 | 8/1989 | Humphries et al. | 435/4 |
| 4,866,168 | 9/1989 | Dougherty et al. | 540/145 |
| 4,883,579 | 11/1989 | Humphries et al. | 204/403 |
| 4,908,442 | 3/1990 | Narang et al. | 540/145 |
| 4,954,416 | 9/1992 | Wright et al. | 430/281 |
| 4,963,815 | 10/1990 | Hafeman | 324/715 |
| 4,977,177 | 12/1990 | Bommer et al. | 540/145 |
| 5,008,043 | 4/1991 | Robello et al. | 252/582 |
| 5,016,063 | 5/1991 | Beratan | 357/8 |
| 5,034,296 | 7/1991 | Ong et al. | 430/59 |
| 5,059,510 | 10/1991 | Jones, Jr. et al. | 540/145 |
| 5,062,693 | 11/1991 | Beratan et al. | 359/241 |
| 5,063,417 | 11/1991 | Hopfield | 357/8 |
| 5,080,764 | 1/1992 | Kester et al. | 204/131 |
| 5,089,545 | 2/1992 | Pol | 524/17 |
| 5,112,934 | 5/1992 | Kester et al. | 528/99 |
| 5,112,977 | 5/1992 | Fischer | 546/195 |
| 5,124,944 | 6/1992 | Suzuki et al. | 365/113 |
| 5,156,810 | 10/1992 | Ribi | 422/82.01 |
| 5,173,546 | 12/1992 | Kester et al. | 525/504 |
| 5,194,361 | 3/1993 | Taguchi | 430/203 |
| 5,202,225 | 4/1993 | Nakamine | 430/566 |
| 5,206,131 | 4/1993 | Matsuda | 430/559 |

OTHER PUBLICATIONS

Science vol. 257, pp. 63–65 "Picosecond Optical Switching Based on Biphotonic Excitation of an Electron Donor–Acceptor–Donor Molecule"–Michael P. O'Neil, et al, 3 Jul. 1992.

Primary Examiner—Mukund J. Shah
Assistant Examiner—Pavanaram K. Sripada
Attorney, Agent, or Firm—Hugh W. Glenn; Robert J. Fisher; William R. Moser

[57] ABSTRACT

A light-intensity dependent molecular switch comprised of a compound which shuttles an electron or a plurality of electrons from a plurality of electron donors to an electron acceptor upon being stimulated with light of predetermined wavelengths, said donors selected from porphyrins and other compounds, and a method for making said compound.

9 Claims, 3 Drawing Sheets

ORGANIC SOLID STATE SWITCHES INCORPORATING PORPHYRIN COMPOUNDS AND METHOD FOR PRODUCING ORGANIC SOLID STATE OPTICAL SWITCHES

CONTRACTUAL ORIGIN OF THE INVENTION

The United States Government has rights in this invention pursuant to Contract Number W-31-109-ENG-38 between the United States Government and Argonne National Laboratory.

BACKGROUND OF THE INVENTION

1. Field of the Invention

The present invention relates to an organic solid state optical "and/or" gate and a method for producing an organic solid state optical "and/or" gate, and specifically an organic solid state optical switch containing a plurality of excited states in selected combinations which may be switched by a plurality of light signals or a combination of light signals and a method for producing said organic solid state optical switch containing a plurality of excited states.

2. Background of the Invention

Basic functions of a computer include information processing and storage. In von Neumann (serial) architectures, those arithmetic, logic, and memory operations are performed by devices that are capable of reversibly switching between two states often referred to as "0" and "1." Semiconducting devices that perform these various functions must be capable of switching between two states at a very high speed using minimum amounts of electrical energy in order to allow the computer to perform basic operations. Transistors perform the basic switching functions in computers.

While the design and production of energy-efficient, state-of-the-art electronic devices depend increasingly on the ability to produce ever higher densities of circuit elements within integrated circuits, semiconductor-based computer technology and architecture have advanced to nearly the quantum mechanical limitations of such configurations. Soon, size and price will limit the use of high-performance computers. The major component that modulates these attributes of high-performance computers is the memory.

Because of the huge data storage requirements of these instruments, a new, compact, low-cost, very high capacity, high speed memory configuration is needed. To reach this objective, molecular electronic switches, wires, microsensors for chemical analysis, and opto-electronic components for use in optical computing are being pursued. The principal advantages of using molecules in these applications are high component density (upwards of $10^{18}$ bits per square centimeter), increased response speeds, and high energy efficiency. If light is used to control molecular devices, many of the quantum statistical problems associated with high packing would be outweighed by pico-second (ps, 1 picosecond=$10^{-12}$ seconds) response times, which are the typical time lapses observed for switching time and relaxation of the predetermined organic material.

Optical transistors, used in the field of molecular optics, perform the same operations as their electronic analogs, but instead of controlling an electrical signal, the optical transistor modulates light. An advantage of all-optical inorganic or organic devices is the elimination of electromagnetic interference or crosstalk that often plagues electronic devices in tightly packed circuits. However, many ionic crystalline materials are more likely to become damaged with laser exposure than are their organic counterparts. The higher resilience of organic materials can be attributed to the high degree of cross-linking found within said complexes. In addition, many organics are more transparent than inorganic optical materials at certain frequencies. An advantage of incorporating organics into optical switches is that the wavelength dependence of transparency of a device can be controlled by synthetic design to match specific laser frequencies.

Optical effects presently developed using organic materials are due to the interaction of light with solutions. Solvent systems are often needed, as in some instances, a particular molecule is not individually switchable in solid state. This solvent effect results from solvent dipoles reorientating around an ion pair in a polar liquid, thereby decreasing the energy of the ion pair, which obviously differs from the situation in solid state wherein solvent dipoles cannot reorient around an ion pair produced. This lack of reorientation produces an energy level of the ion pair that is much higher in rigid matrices than in liquid, so high in fact that the energy requirement lies above the energy of the excited state, in which case photoinduced electron transfer cannot occur.

Disadvantages with solution systems include the presence of solvent interactions and the need for complex device structures. The threshold energies driving these configurations will not suffice in applications requiring solid state switching, as solid state switching requires approximately 0.8 eV (20 kcal) of additional energy compared to solution systems.

Single crystals, polycrystalline films, and amorphous compositions are potential solid state alternatives to solution systems. (See e.g. U.S. Pat. Nos. 4,574,366 and 4,731,756.) However, some of these systems require that heat energy be applied to change illuminated areas from the second state back to the first state. Furthermore, many of the molecular switches heretofore produced have been restricted in use to non-solid state, polar solutions, primarily due to energy limitations.

Other previous attempts to produce chemical switches have yielded switches which manifest a photochromic change concomitant with a change in molecular structure. For example, such photochromic compounds as spiropyrans and aberchrome dyes, each of which have a plurality of stable isomers which exhibit different absorption maxima, have applications in reversible optical memory configurations. These embodiments exhibit relatively slow switching times ranging from millisecond to microsecond durations. As such, photochromic molecules that are based on reversible electron transfer reactions for optical switching should have advantages in both speed and photostability over molecular switches based on photochemical changes in molecular structure.

Other molecular electronic devices, such as that disclosed in U.S. Pat. No. 5,063,417, utilize a chain of electron transfer molecules wherein the information is shifted down a polymer string by photoinduced electron transfer reactions. However, such configurations suffer from not being able to "reset" the initial electron donating moiety from within the compound structure and appear to handle only one electron transfer at a time. Furthermore, the quinones used in such molecular electronic devices are susceptible to irreversible reduction if hydrogen ions are present, thereby not providing the gate function featured in the present invention.

Optical devices based on organic single crystals and polymers exhibit a variety of potentially important optical processes, including but not limited to the following:

Optical bistability,

Optical threshold switching,

Photoconductivity, harmonic generation, optical parametric oscillation, and electro-optic modulation.

In many organic materials, the optical performance and efficiency equals, and in many cases surpasses, that of the best ionic crystalline inorganic materials. The diversity of organic materials also offers greater ease of fabrication and low cost. Organic compounds and polymers allow for control of optical properties of the device by altering the organic molecular structure before beginning the fabrication process. This "molecular architecture" feature simplifies the manufacturing process compared to silicon technologies by reducing the number of device fabrication steps and by locking the optical properties of the device into the molecular structure itself instead of in the processing techniques.

A need exists in the art to produce an organic system to serve as a cornerstone for a "real time" threshold logic element based on the excited state photophysical properties of said organic systems. These chemical switches should be operational in solid states. Such a system must feature high quantum efficiency of photosynthetic charge separation. This high efficiency depends on favorable electron-transfer rates between electron donors and acceptors that are positioned in precise spatial relationships relative to one another and that possess redox potentials which result in movement of an electron down a stepped potential gradient. Other criteria of such an organic molecule system include optical responsivity at common laser wavelengths, low optical threshold powers and processability into device structures.

SUMMARY OF THE INVENTION it is an object of the present invention to provide an organic solid state switch that overcomes many of the disadvantages of the prior art.

Another object of the present invention is to provide a light intensity-dependent molecular switch A feature of the invention is the ability for the switch to be activated by either of two or more light signals or by the combination of light signals. An advantage of the invention is providing extremely fast optical "and" gates measured in pico-seconds.

It is another object of the present invention to provide an organic switch that operates via externally produced dipoles in either solid state or solution. A feature of the invention is the utilization of light wavelengths to induce dipoles. An advantage of the invention is an optical switch relatively immune to the effects of external electromagnetic interference.

Yet another object of the present invention is to provide a light intensity-dependent molecular switch and a method for producing a light intensity-dependent molecular switch. A feature of the invention is the incorporation of porphyrin into the switch. An advantage of the invention is its operability in nonpolar fluids.

Briefly, the invention provides for a light intensity-dependent molecular switch, comprising an electron acceptor moiety having a first end and a second end, a first electron donor moiety attached to the first end of the electron acceptor moiety so to facilitate electron transfer between the first electron donor moiety and the electron acceptor moiety when light of a first predetermined wavelength strikes the first electron donor moiety, thereby creating a first excited state by producing a first ionic couple, and a second electron donor moiety attached to the second end of the electron acceptor moiety so as to facilitate electron transfer between the second electron donor moiety and the electron acceptor moiety when light of a second predetermined wavelength strikes the second electron donor moiety, thereby creating a second excited state by producing a second ionic couple.

The invention also provides for a light intensity-dependent molecular switch comprising N,N'-diphenyl-3,4,9,10-perylenebis (dicarboximide) as an electron acceptor moiety, a porphyrin molecule as a first electron donor moiety and a porphyrin molecule as a second electron donor moiety, both rigidly attached to the electron acceptor moiety, so to facilitate electron transfer between the first and second electron donor moieties and the electron acceptor moiety when light having a first predetermined wavelength strikes the first electron donor moiety, thereby creating a first excited state by producing a first ionic couple and when light of a second predetermined wavelength strikes the second electron donor moiety thereby creating a second excited state by producing a second ionic couple.

Furthermore, the invention provides for a method for producing a light intensity-dependent molecular switch comprising preparing an electron donor moiety by first mixing an aldehyde having a predetermined carbon chain length with p-nitrobenzaldehyde and pyrrole at a first predetermined temperature and for a first predetermined time so as to produce a condensation product, reducing the condensation product, and mixing the now reduced condensation product with an electron acceptor moiety in a 2:1 mole ratio for a second predetermined period of time at a second predetermined temperature sufficient to condense the now reduced condensation product with the electron acceptor.

BRIEF DESCRIPTION OF THE DRAWINGS

The invention and the above and other objects and advantages may best be understood from the following detailed description of the embodiment of the invention shown in the accompanying drawings, wherein.

DETAILED DESCRIPTION OF THE INVENTION

Figure 1:
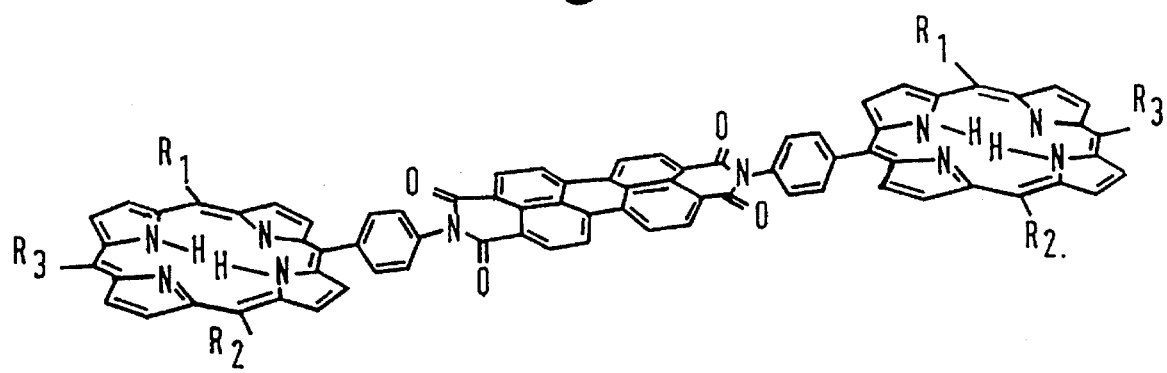
FIG. 1 is a chemical structural formula of a first exemplary light intensity-dependent molecular switch compound illustrating the present invention.

An organic chemical complex is proposed to serve as a cornerstone of a classical bistable optical device. Said device exists in two stable states for a given set of input signals. In such devices, output power increases linearly until a critical threshold value (measured as a predetermined wavelength) is reached. At the threshold point, or first excited state, output jumps sharply (i.e., a nonlinear increase occurs) to a high output regime. At a second threshold point, or second excited state, output again assumes nonlinearity. As input intensity is decreased, the optical input can either return to the low output regime by the same path, or employ a hysteretic loop circuit wherein short-term memory functions can be utilized. Such a device performs signal amplification and basic logic operations such as A/D conversions and "AND" and "OR" functions by simply selecting the appropriate incident beams supplied to it.

These molecules may be used in a variety of media including fluid solution, thin films, polymer fibers and sheets, and organic solids. This invention will function in solids at temperatures down to 4.2° K. Potential applications of this technology are optical computing, i.e. the production of wavelength selective fast gates and switches, laser detectors, and optically-driven electro-optic devices, such as Q-switches (dither switches) for laser modulation and synchronization.

An electron donor-acceptor-donor molecular system has been developed to serve as a light intensity-dependent molecular switch based on a pico-second time scale. Excitation of the electron donor portions of the molecule with subpicosecond laser pulses results in a single (first excited state) or a double reduction (second excited state) of the electron acceptor moiety, depending on light intensity or frequency. As these absorption changes are produced solely by electron transfers, this molecular switch effectively has no moving parts and therefore switches significantly faster than photochromic molecules that must undergo changes in molecular structure.

Such an electron donor-acceptor-donor molecular system is based on two types of molecules, paired with each other based on their reduction potential values. Generally, the sum of the one electron oxidation potential of the donor and the one electron reduction potential of the acceptor must be less than the energy of the lowest excited singlet state, as depicted in Equation 1 below:

$$\Delta G = -(E_S - E_D - E_A)$$ (Equation 1)

wherein $E_S$ is the energy of the lowest excited singlet state of the donor, $E_D$ is the half cell potential of the donor, and EA is the half cell potential of the acceptor. Essentially, the free energy of this reaction at the lowest excited state is always negative, with redox occurring at predetermined, sharply defined light wavelengths. Any stable reference electrode whose potential is known can be used to determine the value of either half reaction. The inventors used the standard calomel electrode to measure the potential of the following molecular system examples.

Aside from negative $\Delta G$ values, another criterion is that the acceptor also must be capable of accepting one or two electrons reversibly.

Donor- and Acceptor-Moiety Detail

Generally, the molecular switches proposed herein are made possible by pairing a suitable set of electron donor molecules with an electron acceptor molecule based upon their relative oxidation-reduction potentials. There are a myriad of electron donors that can be utilized in the instant molecular switch design, including but not limited to porphyrins, substituted porphyrins, β-carotenes, β-carotene derivatives, phthalocyanines, carbazoles, phenylenediammine, and combinations thereof. The inventors have found, for example, that a donor comprised of porphyrin substituted with zinc and/or magnesium significantly increases the free energy ($\Delta G$) available, thereby facilitating easier transfer of an electron. However, some heavier metal substitutions, using nickel for example, produce triplet excited states, leading to a too rapid deactivation rate. Typical deactivation rates occur in nanosecond time durations.

Generally, any electron donor with a half cell potential less positive than 1.4 V is a suitable moiety.

Many compounds having good oxidation characteristics can be utilized as the electron acceptor moiety. For example, a myriad of compounds can be utilized as electron acceptors, including benzoquinone, naphthoquinone, and a variety of aromatic diimides, including but not limited to N,N'-diphenyl-3,4,9,10-perylenebis (dicarboximide), also called PBDCl, 1,4,5,8-naphthalene diimide, 1,2,4,5-benzene diimide (pyrrole-mellitic diimide), 2,3,6,7 naphthalene diimide, and combinations thereof. In two particular compounds, wherein PBDCl is used as the electron acceptor, namely compound 1 depicted in FIG. 1 as N,N'-bis(5-(4-aminophenyl)-10,15,20-tripentylporphyrin)-3,4,9,10-perylene-bis (dicarboximide), and compound 2 depicted in FIG. 2 as N-(5-(4-aminophenyl)-10,15,20-tripentylporphyrin)-N'-(2-amino-9,10(1,2-benzeno)anthracene)-3,4,9,10-perylene-bis(dicarboximide), elaborated on below in the samples section, the heretofore poor performance of porphyrins as electron donors in nonpolar solvents is outweighed by PBDCl's extreme disposition to be reduced. Another advantage of using PBDCl is its ability to readily accept two electrons in sequence, with both excited state moieties absorbing light at two different regions of the spectrum.

Solid State and Solution Media

A variety of solutions and substrates can be used to support the invented compounds, including but not limited to polymethylmethacrylate films, liquid crystal polymers, self assembled monolayers on gold, covalent attachment to silicon based materials including silicon itself and glass, and combinations thereof. Said compounds exhibit optical switching characteristics as mentioned above in either solid or liquid state and in concentrations ranging from between approximately $10^{-7}$ to $10^{-4}$ molar. Solubilities of the invented compound will vary also, depending on the alkyl groups substituted on the electron donor portion of the molecule. For example, while solubility of porphyrins are generally limited, such solubilities can be increased by selecting the carbon chain length from between approximately C-6 to C-15. Of course, and as mentioned supra, a concomitant change in condensation reactants in the initial formulation of porphyrin would be required. For example, when changing from a pentyl substituted moiety to a C-15 substituted moiety on the porphyrin, hexadecanal would be used instead of hexanal as a reactant in the Lindsey and Wagner treatment, referenced below.

Compound Examples 1 and 2

An electron donor-acceptor-donor molecule has been invented, consisting of two free-base meso-tripentyl-monophenylporphyrins (HP) rigidly attached to N,N'-diphenyl-3,4,9,10-perylenebis (dicarboximide) (PBDCl), that exhibits light intensity-dependent optical switching by means of two ultrafast electron-transfer reactions.

Figure 2:
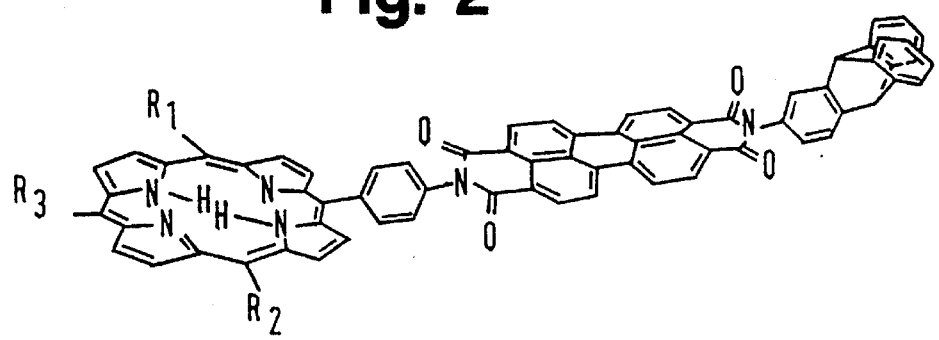
FIG. 2 is a chemical structural formula of a second exemplary light intensity-dependent molecular switch illustrating the present invention.

Compounds depicted as FIGS. 1 and 2 were prepared in three steps:

Meso-trialkyl-mono (p-nitrophenyl) porphyrin was prepared by condensing a 05-0-15 aldehyde (i.e., R=an aldehyde with a carbon length selected from the range of approximately 5 carbons to 15 carbons) with p-nitrobenzaldehyde, and pyrrole under the conditions established by Lindsey and Wagner (*J. Org. Chem.* 54, 828 (1989)). Condensation temperatures and times can range from 20° to 40° C. and 15 to 180 minutes, respectively.

The porphyrin was reduced to meso-trialkyl (p-aminophenyl) porphyrin with $SnCl_2$ in tetrahydrofuran-aqueous HCl. Aside from the tin compound, other more typical reducing agents can be employed, including but not limited to hydrogen over platinum or palladium catalyst, hydrazine in ethanol with palladium catalyst, and combinations thereof.

Two moles of the aminophenylporphyrin were condensed with 1 mol of perylenetetra-carboxydianhydride (Aldrich) in molten imidazole at 170° C. in the presence of Linde 3A (3 Å) molecular sieves for 30 minutes. Condensation temperatures selected from a range of approximately 100° C. to 200° C. can be utilized. Furthermore, a reaction time of between 15 minutes and 60 minutes, depending on condensation temperature, yields good results.

Aqueous work-up followed by chromatography on silica gel gave compound 1 in 35 percent yield. Compound 2 was produced in 20 percent yield by using 1 mol each of the porphyrin, 2-aminotriptycene, and perylenetetracarboxydianhydride. Other amines can be used to increase solubility, such as any amine with the $NH_2$ attached to a secondary carbon site, as seen with amino acids and their derivatives, including ethyl leucine.

The solubility of PBDCl derivatives depends on adding substituents at the nitrogens that sterically inhibit stacking of the PBDCl rings. 2-aminotriptycene fulfills this requirement while retaining the reactivity of an ordinary aniline in the condensation reaction. The resulting statistical mixture of bis (dicarboximides) was easily separated chromatographically.

Reduction Potential Detail

The PBDCl derivatives embodied in Compounds 1 and 2 can be reversibly reduced with either one or two electrons at thermodynamic half-wave potentials $E_{1/2}-=-0.50$ V and $E_{1/2}2-=-0.73$ V versus a saturated calomel electrode in pyridine, while $E_{1/2}+$ for one-electron oxidation of the porphyrin is 0.92 V. These data, and the following equation 2 below show that PBDCl is an excellent electron acceptor:

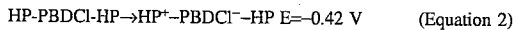

HP-PBDCl-HP→HP$^+$-PBDCl$^-$-HP  E=-0.42 V    (Equation 2)

The PBDCl$^-$ and PBDCl$^{2-}$ ions have characteristic intense optical absorptions at 713 and 546 nm, respectively. This opens up the possibility that rapid, photoinduced electron transfers from donor molecules may be used to selectively reduce PBDCl with either one or two electrons. The resultant photochromic changes in absorption from 713 to 546 nm could form the basis for molecular switches based on optimized molecular absorption characteristics.

Photoinduced reduction of PBDCl by the lowest excited singlet state of HP was detected readily with transient optical absorption spectroscopy. Pyridine solutions ($5 \times 10^{-5}$M) of compounds 1 and 2 depicted in FIGS. 1 and 2, wherein $R_1$, $R_2$ and $R_3$ were all pentyl groups, were excited with 160 femto-second (fs, 1 fs=$10^{-5}$ seconds) laser pulses at 585 nm with a 1 kHz repetition rate. The optical absorbances of the samples at 585 nm were 0.3 and were limited by the solubility of these compounds in pyridine. Time-resolved transient absorption spectra of compounds 1 and 2 after excitation were monitored with a femtosecond white light continuum. The overall instrumental response was 200 fs, the diameter of the excitation beam in the sample was 0.2 ram, and the path lengths of the collinear excitation and probe beams through the stirred sample were 1 cm.

Figure 3:
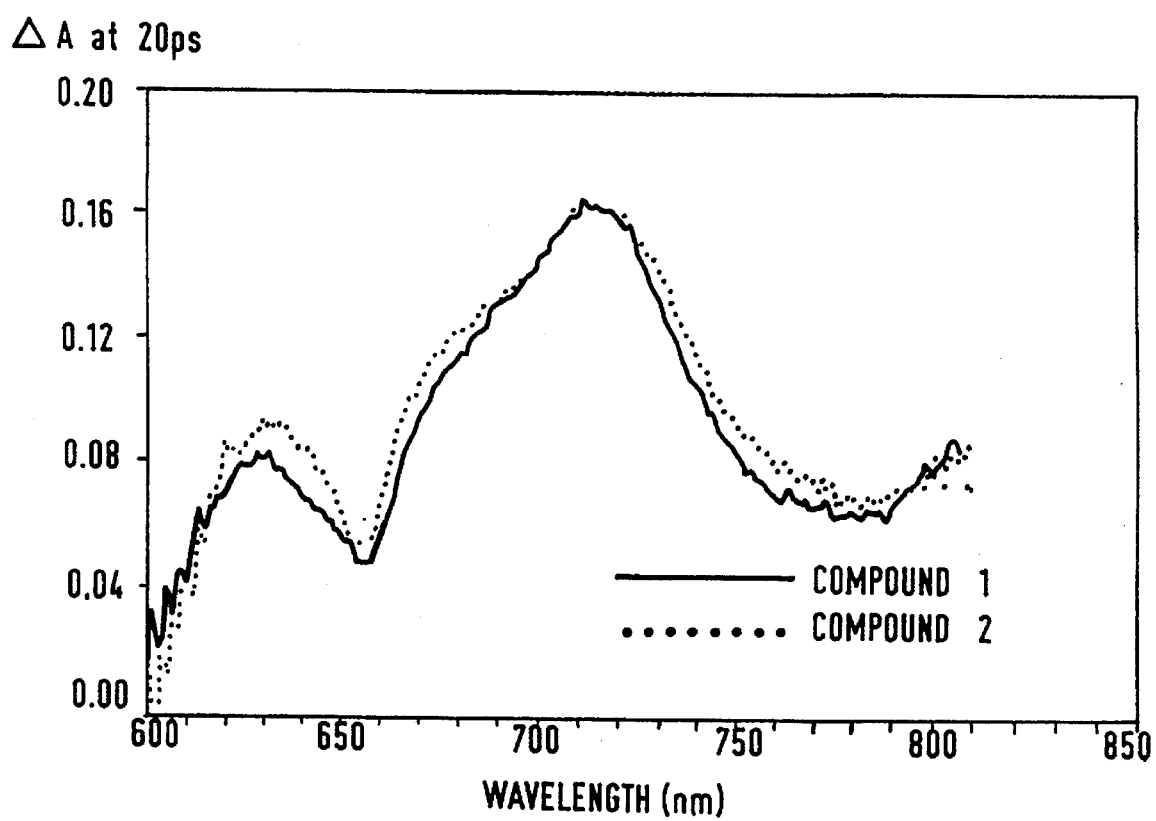
FIG. 3 is an absorption spectrum depicting single photon excitation of the first and second compounds depicted in FIGS. 1 and 2 at 713 nm, illustrating the present invention.

The transient spectra in FIG. 3 show that single photon excitation for 20 picoseconds (ps) of both compounds 1 and 2 results in formation of HP$^+$-PBDCl$^-$, as characterized by the intense absorption of PBDCl- at 713 nm.

Dipole Durations

The lifetime of HP$^+$-PBDCl$^-$ in both compounds 1 and 2 was measured as a function of laser excitation intensity up to 15 µJ per pulse ($1.4 \times 10^{17}$ photons per centimeter square, 20 photons per molecule) available to the inventors. Surprisingly and unexpectedly, it was found that the lifetime of HP$^+$-PBDCl$^-$ ion pair in compound 2 was independent of excitation intensity, whereas the lifetime of the same ion pair in compound 1 decreases as the laser intensity increases, reaching a value that saturates at about half the lifetime of the ion pair in compound 2. In addition, at high light intensities the rate constant for formation of HP$^+$-PBDCl$^-$ within compound 1 increases to $2.0\pm0.2\times10^{11}$ s$^{-1}$, while that for compound 2 remains constant.

Figure 4:
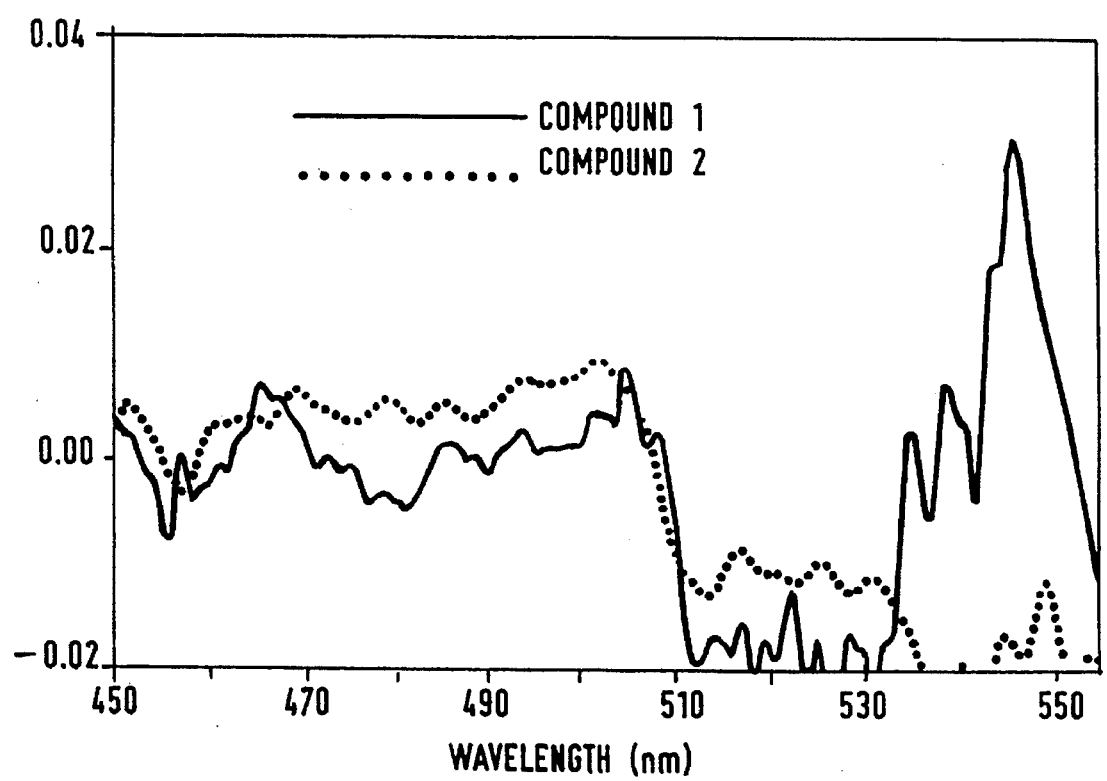
FIG. 4 is an absorption spectrum depicting the doubly reduced electron acceptor at 546 nm, illustrating the present invention.

At 713 nm, another process is competitive with the formation of HP$^+$-PBDCl$^-$-HP, namely, the formation of HP$^+$-PBDCl$^{2-}$-HP$^+$. At these intensities, the 160-fs duration of the excitation flash ensures that both porphyrins within compound 1 are excited simultaneously. Two photon excitation of compound 1 provides 3.8 eV available to facilitate rapid electron transfer from one of the porphyrins, having the rate constant mentioned supra. While singlet-singlet annihilation is another potential pathway for deactivation, the ten fold decrease in the annihilation rate ($<2\times10^{10}$ s$^{-1}$) compared with the already discussed rate constant is indicative that this mechanism probably contributes little to transfer. Furthermore, the total transient absorption change at 546 nm for either 2HP$^+$, or both HP$^+$ and HP$^-$ is one-fifth that of the absorption of PBDCl$^{2-}$. The absorption spectra for the doubled reduced acceptor is depicted in FIG. 4, wherein the light intensity of 20 photons per molecule was applied for 300 ps. In summary, singlet-singlet annihilation may be disfavored by electronic coupling considerations, even though the free energy of reaction for the production of HP$^+$-PBDCl-HP$^+$ is favorable. The ion pairs within the charged-separated species HP$^+$-PBDCl$^{2-}$-HP$^+$ recombine on approximately a 5-ns time scale. The long lifetime of these ion pairs is consistent with the so-called inverted-region behavior of electron-transfer reactions involving high energy ion pairs.

The photophysical behavior of compound 1 constitutes a light intensity-dependent optical switch. As the light intensity is increased, compound 1 switches from being a strong transient absorber at 713 nm to an absorber at 546 nm. Such molecules could be used to modulate two light beams at different colors on a picosecond time scale. Compound 1 can use two different excitation wavelengths in the switching. As the PBDCl molecule absorbs strongly at 526 nm and possesses a 2.3-eV lowest excited singlet state, excitation of PBDCl will initiate the first electron transfer to produce HP$^+$-PBDCl$^-$-HP. The second electron transfer may be initiated by application of a second photon, at 585 nm, that is absorbed principally by the remaining ground-state porphyrin. Therefore, compound 1 should be able to perform logic operations.

Generally, light wavelengths of between 400 and 800 nm will induce a change from ground state to excited state in the molecules described above.

While the invention has been described with reference to details of the illustrated embodiment, these details are not intended to limit the scope of the invention as defined in the appended claims.

The embodiment of the invention in which an exclusive property or privilege is claimed is defined as follows:

1. A light intensity-dependent molecular switch comprising:

an aromatic diimide having a first end and a second end, said ends terminating with identical chemical structures;

a first electron donor selected from the group consisting of porphyrin and substituted porphyrin, said first electron donor covalently attached to the first end of the diimide so to facilitate reversible electron transfer between the first electron donor and the diimide when light of a first predetermined wavelength strikes the first electron donor, thereby creating a first excited state; and anthracene covalently attached to the second end of the diimide so as to facilitate reversible electron transfer between the anthracene and the diimide when light of a second predetermined wavelength strikes the anthracene, thereby creating a second excited state.

2. The invention as recited in claim 1 wherein the substituted porphyrin is metallated with metals selected from the group consisting of Zn, Mg, and combinations thereof.

3. The invention as recited in claim 1 wherein the substituted porphyrin is substituted with alkyl groups ranging in carbon length from approximately 5 carbons to 15 carbons.

4. The invention as recited in claim 1 wherein the aromatic diimide is selected from the group consisting of N,N'-diphenyl-3,4,9,10-perylene (dicarboximide), 1,4,5,8-naphthalene diimide, 1,2,4,5-benzene diimide, 2,3,6,7-naphthalenediimide, and combinations thereof.

5. The invention as recited in claim 1 wherein the first predetermined light wavelength and the second predetermined light wavelength are selected from the range of between approximately 400 nm and 800 nm.

6. A light intensity-dependent molecular switch consisting of:

N,N'-diphenyl-3,4,9,10-perylenebis (dicarboximide) as an electron acceptor moiety;

a porphyrin molecule as a first electron donor moiety and a porphyrin molecule as a second electron donor moiety, both covalently attached to the electron acceptor moiety, so to facilitate reversible electron transfer between the first and second electron donor moieties and the electron acceptor moiety when light having a first predetermined wavelength strikes the first electron donor moiety, thereby creating a first excited state and when light of a second predetermined wavelength strikes the second electron donor moiety thereby creating a second excited state.

7. The invention as recited in claim 6 wherein the porphyrin molecule is metallated with a metal selected from the group consisting of Zn, Mg, and combinations thereof.

8. The invention as recited in claim 6 wherein the first predetermined light wavelength is 713 nm and the second predetermined light wavelength is 546 nm.

9. The invention as recited in claim 6 wherein the porphyrin molecule is substituted with a plurality of alkyl groups ranging in carbon chain length from 5 to 15 carbons.

* * * * *